United States Patent
Hashimoto et al.

(10) Patent No.: US 6,982,275 B2
(45) Date of Patent: Jan. 3, 2006

(54) PROCESS FOR PRODUCING OPTICALLY ACTIVE SULFOXIDE DERIVATIVE

(75) Inventors: Hideo Hashimoto, Kobe (JP); Tadashi Urai, Takatsuki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/276,109

(22) PCT Filed: Apr. 26, 2001

(86) PCT No.: PCT/JP01/03613

§ 371 (c)(1),
(2), (4) Date: Oct. 24, 2002

(87) PCT Pub. No.: WO01/83473

PCT Pub. Date: Nov. 8, 2001

(65) Prior Publication Data

US 2003/0171591 A1    Sep. 11, 2003

(30) Foreign Application Priority Data

Apr. 28, 2000  (JP) .............................. 2000-128760

(51) Int. Cl.
| A61K 31/4439 | (2006.01) |
| A61K 31/4184 | (2006.01) |
| A61K 31/44 | (2006.01) |
| C07D 209/30 | (2006.01) |
| C07D 401/12 | (2006.01) |
| C07D 235/28 | (2006.01) |

(52) U.S. Cl. ...................... 514/339; 514/339; 514/418; 546/273.4; 546/277.4; 548/307.1; 548/486

(58) Field of Classification Search ............. 546/277.1, 546/273.4, 277.4; 514/339, 418; 548/307.1, 548/486
See application file for complete search history.

(56) References Cited

FOREIGN PATENT DOCUMENTS

| EP | 119 1025 | 3/2002 |
| JP | 2000 016992 | 1/2000 |
| WO | WO 96/02535 | 2/1996 |
| WO | WO-96/02535 | * 2/1996 | .............. 546/273.4 |
| WO | WO 96/17076 | 6/1996 |
| WO | WO 00/78745 | 12/2000 |
| WO | WO 01/14366 | 3/2001 |

OTHER PUBLICATIONS

Donnoli, Maria et al. "Catalytic Asymmetric Oxidation of Aryl Sulfides with a Ti/H20/ (R,R)-Diphenylethane-1,2-diol Complex: a Versatile and Highly Enantioselective Oxidation Protocol." J. Org. Chem. 1998, vol. 63, pp. 9392-9395.*

(Continued)

Primary Examiner—Kamal A. Saeed
Assistant Examiner—Janet L. Coppins
(74) Attorney, Agent, or Firm—Elaine M. Ramesh; Mark Chao

(57) ABSTRACT

The present invention relates to a production method of an optically active form of a compound represented by formula (II)

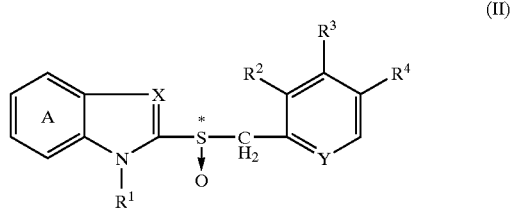

wherein ring A is a benzene ring optionally having substituent(s); $R^1$ is H, a hydrocarbon group optionally having substituent(s), an acyl group or an acyloxy group; $R^2$, $R^3$ and $R^4$ are each H, an alkyl group optionally having substituent(s), an alkoxy group optionally having substituent(s) or an amino group optionally having substituent(s); X is N or CH; Y is N or CH; and * shows an asymmetric center, or a salt thereof, which includes reacting a compound represented by the formula (I)

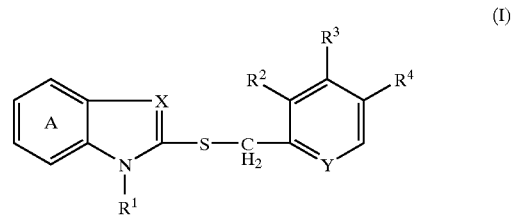

wherein each symbol is as defined above, or a salt thereof, with an excess amount of an oxidizing agent in the presence of a catalyst for asymmetric induction, and provides an efficient production method of an optically active sulfoxide derivative in high yield on an industrial large scale by a convenient method, while achieving an extremely high enantiomer excess.

13 Claims, No Drawings

OTHER PUBLICATIONS

Donnoli et al, Catalytic Asymmetric Oxidation of Aryl Sulfides with a Ti/H2O/(R,R)-Diphenylethane-1,2-diol Complex: a Versatile and Highly Enantioselective Oxidation Protocol. J. Org. Chem. 1998, vol. 63 No. 25, pp. 9392-9395.*

Donnoli, Maria et al. "Catalytic Asymmetric Oxidation of Aryl Sulfides with a Ti/H2O/(R,R)-Diphenylethane-1,2-diol Complex," J. Org. Chem. (1998), vol. 63, pp 9392-9395.*

Cotton et al. "Asymmetric Synthesis of Esomeprazole" Tetrahedron:Asymmetry 11: 3819-3825 (2000).

Pitchen, P., et al., An Efficient Asymmetric Oxidation of Sulfides to Sulfoxides, *J. Am. Chem. Soc.*, (1984), vol. 106, No. 26, pp. 8188-8193.

\* cited by examiner

PROCESS FOR PRODUCING OPTICALLY ACTIVE SULFOXIDE DERIVATIVE

This application is the National Phase filing of International Patent Application No. PCT/JP01/03613, filed Apr. 26, 2001.

TECHNICAL FIELD

The present invention relates to a production method of an optically active sulfoxide derivative having an antiulcer activity.

BACKGROUND ART

An optically active sulfoxide derivative having an antiulcer activity can be obtained by asymmetric oxidization of a prochiral sulfide derivative. Generally, the above-mentioned reaction produces sulfone, which is an excess reaction product. As a result, the obtained sulfoxide derivative comprises, as analogous substances, unreacted sulfide derivatives and sulfone derivatives as excess reaction products.

As a production method for obtaining an optically active sulfoxide derivative, for example, WO 96/02535 (Japanese Patent Application under PCT laid-open under kohyo No. Hei 10-504290) discloses a method comprising reacting a sulfide derivative and an oxidizing agent in an organic solvent in the presence of a chiral titanium complex and a base to give an optically active sulfoxide compound.

For example, in Example 22 of this publication, it is described that a mixture, which was obtained by adding water (3.6 mmol), (+)-diethyl L-tartrate (15.0 mmol) and titanium(IV) isopropoxide (6.0 mmol) to a solution of 2-[[[3-methyl-4-(2,2,2-trifluoroethoxy)-2-pyridinyl]methyl]thio]-1H-benzimidazole (6.0 mmol) in toluene, stirring the resulting mixture at 50° C. for 60 min, cooling the reaction mixture to room temperature, adding N,N-diisopropylethylamine (6.0 mmol) and cumene hydroperoxide (6.0 mmol) and stirring the mixture at room temperature for 16 hr, consisted of 13% of sulfide, 8% of sulfone and 76% of sulfoxide as determined by achiral HPLC, that post-treatments of purification by flash chromatography and the like gave (+)-2-[[[3-methyl-4-(2,2,2-trifluoroethoxy)-2-pyridinyl]methyl]sulfinyl]-1H-benzimidazole (0.85 g) showing 46%ee enantiomer excess, and that, by further purification, 0.31 g (14%) of the objective substance having an optical purity of 99.6%ee was ultimately obtained as an oily substance.

JP-A-2000-16992 discloses a method for obtaining a sulfoxide compound, which comprises oxidizing a particular thioether compound with N-halosuccinimide, 1,3-dihalo-5,5-dimethylhydantoin or dichlorocyanuric acid salt in the presence of a base. It further teaches that, depending on the reaction conditions, the reaction may not terminate with the production of sulfoxide and a side reaction may occur, wherein a part of the resulting sulfoxide is further oxidized into sulfone, and production of sulfone decreases the yield of the objective sulfoxide, and that because the physical and chemical properties of the both are extremely similar, their separation and purification is difficult.

Conventional production methods are associated with the problems that a sulfone form, which is difficult to remove, is produced, that the objective optically active sulfoxide form has a low optical purity (enantiomer excess), thus essentially requiring purification by column chromatography and the like, and that the yield is low. In view of the above, a production method of an optically active sulfoxide derivative having an antiulcer activity is desired, which is industrially advantageous from the aspects of amount of analogous substances present therein, optical purity, yield, productivity and economic aspect.

DISCLOSURE OF THE INVENTION

Generally, in this kind of oxidation reaction, an excess reaction, i.e., production of sulfone derivative, is suppressed by decreasing the amount of the oxidizing agent to be used. For example, in all the Examples (Examples 1–29) of Japanese Patent Application under PCT laid-open under kohyo No. Hei 10-504290, the amount of the oxidizing agent to be used is 0.9 to 1.1 molar equivalents relative to the starting material, and the amount of the sulfone derivative present in the obtained reaction mixture is 1.2 to 8.8%.

However, the present inventors have studied the production method of an optically active sulfoxide derivative from various aspects, and unexpectedly found for the first time that an oxidization reaction using an excess oxidizing agent at a temperature lower than room temperature results in strikingly low level production of sulfone derivative, a strikingly low residual ratio of sulfide derivative, and production of an optically active sulfoxide derivative having an extremely high optical purity in a high yield, based on which finding they have intensively studied and completed the present invention.

Accordingly, the present invention relates to

[1] a method for producing an optically active form of a compound represented by the formula (II):

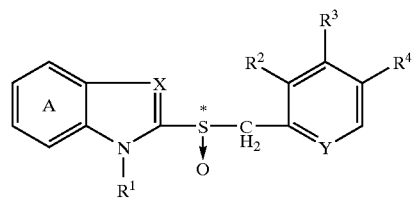

wherein
ring A is a benzene ring optionally having substituent(s),
$R^1$ is a hydrogen atom, a hydrocarbon group optionally having substituent(s), an acyl group or an acyloxy group,
$R^2$, $R^3$ and $R^4$ are each a hydrogen atom, an alkyl group optionally having substituent(s), an alkoxy group optionally having substituent(s) or an amino group optionally having substituent(s),
X is a nitrogen atom or CH,
Y is a nitrogen atom or CH, and
* is an asymmetric center, or a salt thereof [hereinafter sometimes to be briefly referred to as compound (II)], comprising reacting a compound represented by the formula (I):

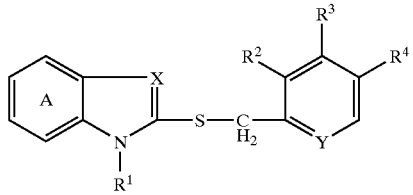

wherein each symbol is as defined above, or a salt thereof [hereinafter sometimes to be briefly referred to as compound (I)] with an excess amount of an oxidizing agent in the presence of a catalyst for asymmetric induction;

[2] the method according to the above-mentioned [1], wherein the amount of the oxidizing agent to be used is about 1.5 to about 10 molar equivalents relative to compound (I);

[3] the method according to the above-mentioned [1], wherein the amount of the oxidizing agent to be used is about 2.5 to about 4 molar equivalents relative to compound (I);

[4] the method according to the above-mentioned [1], wherein the reaction is carried out at about −20° C. to about 20° C.;

[5] the method according to the above-mentioned [1], wherein the reaction is carried out at about −10° C. to about 10° C.;

[6] the method according to the above-mentioned [1], wherein the catalyst for the asymmetric induction is an optically active titanium composite;

[7] the method according to the above-mentioned [1], wherein the composite is a complex comprising an optically active diol, titanium(IV) alkoxide and water;

[8] the method according to the above-mentioned [7], wherein the complex is formed using the titanium(IV) alkoxide/optically active diol/water in a molar ratio of 1/about 1-about 10/about 0.1-about 2;

[9] the method according to the above-mentioned [7], wherein the amounts of the titanium(IV) alkoxide and the oxidizing agent are used in an amount of about 0.03 to about 1 molar equivalent and about 1.5 to about 10 molar equivalents, respectively, relative to 1 molar equivalent of the compound represented by the formula (I) or a salt thereof, and the reaction is carried out at about −20° C. to about 20° C.;

[10] the method according to the above-mentioned [1], wherein the reaction is carried out in the presence of a base;

[11] the method according to the above-mentioned [1], wherein the compound represented by the formula (II) is a compound represented by the formula:

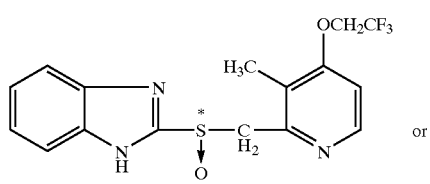 or

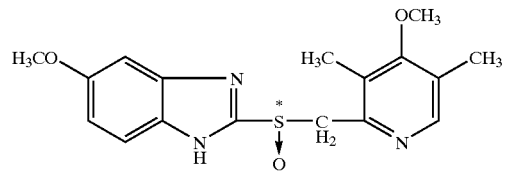

; and the like.

BEST MODE FOR EMBODYING THE INVENTION

The compound (II) has a sulfur atom to be an asymmetric center and includes the following two kinds of optical isomers.

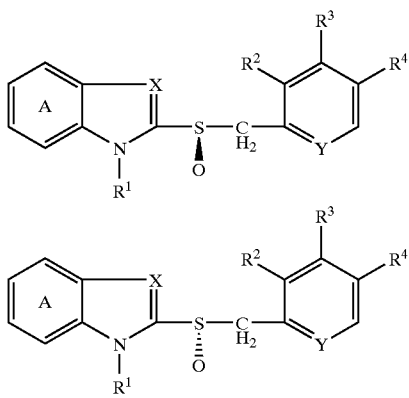

In the above-mentioned formulas, the "substituent" of the "benzene ring optionally having substituent(s)" represented by ring A includes, for example, 1 to 3 of a halogen atom, a cyano, a nitro, an alkyl optionally having substituent(s), a hydroxy, an alkoxy optionally having substituent(s), an aryl, an aryloxy, a carboxy, an acyl, an acyloxy, a 5 to 10-membered heterocyclic group and the like. When the number of substituents is 2 or more, each substituent may be the same or different. Of these, a halogen atom, an alkyl optionally having substituent(s), an alkoxy optionally having substituent(s) and the like are preferable.

Examples of the halogen atom include fluorine, chlorine, bromine and the like. Of these, fluorine is preferable.

The "alkyl" of the "alkyl optionally having substituent(s)" is, for example, a $C_{1-7}$ alkyl (e.g., methyl, ethyl, propyl, isopropyl, butyl, isobutyl, sec-butyl, tert-butylpentyl, hexyl, heptyl etc.). The "substituent" of the "alkyl optionally having substituent(s)" includes, for example, 1 to 3 of a halogen atom, a hydroxy, a $C_{1-6}$ alkoxy (e.g., methoxy, ethoxy, propoxy, butoxy etc.), a $C_{1-6}$ alkoxycarbonyl (e.g., methoxycarbonyl, ethoxycarbonyl, propoxycarbonyl etc.), a carbamoyl and the like. When the number of substituents is 2 or more, each substituent may be the same or different.

Examples of the "alkoxy" of the "alkoxy optionally having substituent(s)" include a $C_{1-6}$ alkoxy (e.g., methoxy, ethoxy, propoxy, isopropoxy, butoxy, isobutoxy, pentoxy etc.) and the like. The "substituent" of the "alkoxy optionally having substituent(s)" is exemplified by the same number of the same substituents as those recited above with regard to the "substituent" of the "alkyl optionally having substituent(s)".

Examples of the "aryl" include a $C_{6-14}$ aryl (e.g., phenyl, 1-naphthyl, 2-naphthyl, biphenylyl, 2-anthryl etc.) and the like.

Examples of the "aryloxy" include a $C_{6-14}$ aryloxy (e.g., phenyloxy, 1-naphthyloxy, 2-naphthyloxy etc.) and the like.

Examples of the "acyl" include formyl, alkylcarbonyl, alkoxycarbonyl, carbamoyl, alkylcarbamoyl, alkylsulfinyl, alkylsulfonyl and the like.

Examples of the "alkylcarbonyl" include a $C_{1-6}$ alkylcarbonyl (e.g., acetyl, propionyl etc.) and the like.

Examples of the "alkoxycarbonyl" include a $C_{1-6}$ alkoxycarbonyl (e.g., methoxycarbonyl, ethoxycarbonyl, propoxycarbonyl, butoxycarbonyl etc.) and the like.

Examples of the "alkylcarbamoyl" include an N-$C_{1-6}$ alkylcarbamoyl (e.g., methylcarbamoyl, ethylcarbamoyl etc.), an N,N-diC$_{1-6}$ alkyl-carbamoyl (e.g., N,N-dimethylcarbamoyl, N,N-diethylcarbamoyl etc.) and the like.

Examples of the "alkylsulfinyl" include a $C_{1-7}$ alkylsulfinyl (e.g., methylsulfinyl, ethylsulfinyl, propylsulfinyl, isopropylsulfinyl etc.).

Examples of the "alkylsulfonyl" include a $C_{1-7}$ alkylsulfonyl (e.g., methylsulfonyl, ethylsulfonyl, propylsulfonyl, isopropylsulfonyl etc.).

Examples of the "acyloxy" include alkylcarbonyloxy, alkoxycarbonyloxy, carbamoyloxy, alkylcarbamoyloxy, alkylsulfinyloxy, alkylsulfonyloxy and the like.

Examples of the "alkylcarbonyloxy" include a $C_{1-6}$ alkylcarbonyloxy (e.g., acetyloxy, propionyloxy etc.) and the like.

Examples of the "alkoxycarbonyloxy" include a $C_{1-6}$ alkoxycarbonyloxy (e.g., methoxycarbonyloxy, ethoxycarbonyloxy, propoxycarbonyloxy, butoxycarbonyloxy etc.) and the like.

Examples of the "alkylcarbamoyloxy" include a $C_{1-6}$ alkylcarbamoyloxy (e.g., methylcarbamoyloxy, ethylcarbamoyloxy etc.) and the like.

Examples of the "alkylsulfinyloxy" include a $C_{1-7}$ alkylsulfinyloxy (e.g., methylsulfinyloxy, ethylsulfinyloxy, propylsulfinyloxy, isopropylsulfinyloxy etc.).

Examples of the "alkylsulfonyloxy" include a $C_{1-7}$ alkylsulfonyloxy (e.g., methylsulfonyloxy, ethylsulfonyloxy, propylsulfonyloxy, isopropylsulfonyloxy etc.).

The "5- to 10-membered heterocyclic group" may be a 5- to 10-membered (preferably 5- or 6-membered) heterocyclic group containing, besides carbon atom, one or more heteroatom(s) (e.g., 1–3) selected from nitrogen atom, sulfur atom and oxygen atom, which is exemplified by 2- or 3-thienyl, 2-, 3- or 4-pyridyl, 2- or 3-furyl, 1-, 2- or 3-pyrrolyl, 2-, 3-, 4-, 5- or 8-quinolyl, 1-, 3-, 4- or 5-isoquinolyl, 1-, 2- or 3-indolyl and the like. Of these, preferred is a 5- or 6-membered heterocyclic group such as 1-, 2- or 3-pyrrolyl and the like.

Preferable examples of the ring A include a benzene ring optionally having 1 or 2 substituents selected from halogen atom, optionally halogenated $C_{1-4}$ alkyl, optionally halogenated alkoxy and 5- or 6-membered heterocyclic group.

The group represented by the formula

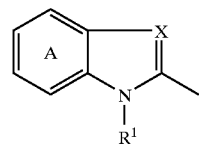

wherein each symbol is as defined above, is preferably a group represented by the formula

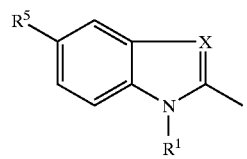

wherein $R^5$ is a hydrogen atom, an optionally halogenated $C_{1-4}$ alkyl, an optionally halogenated alkoxy or 5- or 6-membered heterocyclic group and $R^1$ is as defined above. $R^5$ is preferably (1) a hydrogen atom, (2) an optionally halogenated $C_{1-3}$ alkoxy or (3) 1-, 2- or 3-pyrrolyl.

The "hydrocarbon group" of the "hydrocarbon group optionally having substituent(s)" represented by $R^1$ is, for example, a straight chain, branched chain or cyclic aliphatic hydrocarbon group optionally having a double bond or triple bond, an aryl group, an aralkyl group and the like. Specific examples thereof include alkyl group, alkenyl group, alkynyl group, aryl group, aralkyl group and the like, with preference given to $C_{1-19}$ hydrocarbon group and the like.

Preferable examples of the alkyl group include a straight chain or branched chain alkyl group having 1 to 6 carbon atoms and a cyclic alkyl group having 3 to 14 carbon atoms. For example, $C_{1-6}$ alkyl group and $C_{3-14}$ cycloalkyl group, such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl, cyclohexyl and the like, and the like are used.

Preferable examples of the alkenyl group include a straight chain or branched chain alkenyl group having 2 to 6 carbon atoms and a cyclic alkenyl group having 3 to 14 carbon atoms. For example, $C_{2-6}$ alkenyl groups and $C_{3-14}$ cycloalkenyl groups such as allyl, isopropenyl, isobutenyl, 2-pentenyl, 2-hexenyl, 2-cyclohexenyl and the like, and the like are used.

Preferable examples of the alkynyl group include an alkynyl group having 2 to 6 carbon atoms. For example, $C_{2-6}$ alkynyl groups such as propargyl, 2-butynyl, 3-butynyl, 3-pentynyl, 3-hexynyl and the like, and the like are used.

Preferable examples of the aryl group include an aryl group having 6 to 14 carbon atoms. For example, phenyl, naphthyl, anthryl and the like are used.

Preferable examples of the aralkyl group include an aralkyl group having 7 to 19 carbon atoms. For example, phenyl-$C_{1-4}$ alkyl such as benzyl, phenethyl, phenylpropyl and the like, benzhydryl, trityl and the like are used.

When the above-mentioned hydrocarbon group is an alkyl group, an alkenyl group or an alkynyl group, it may be substituted by 1 to 3 of an alkylthio group (e.g., $C_{1-4}$ alkylthio such as methylthio, ethylthio, n-propylthio, isopropylthio etc., and the like), a halogen (e.g., fluorine, chlorine, bromine, iodine), an alkoxy group (e.g., $C_{1-6}$ alkoxy such as methoxy, ethoxy, n-propoxy, tert-butoxy, n-hexyloxy etc. and the like), an acyloxy group [e.g., $C_{1-6}$ alkyl-carbonyloxy (e.g., acetyloxy, propionyloxy etc.), $C_{1-6}$ alkoxy-carbonyloxy (e.g., methoxycarbonyloxy, ethoxycarbonyloxy, propoxycarbonyloxy, butoxycarbonyloxy etc.), $C_{1-6}$ alkyl-carbamoyloxy (e.g., methylcarbamoyloxy, ethylcarbamoyloxy etc.), $C_{1-7}$ alkylsulfinyloxy (e.g., methylsulfinyloxy, ethylsulfinyloxy, propylsulfinyloxy, isopropylsulfinyloxy etc.), $C_{1-7}$ alkylsulfonyloxy (e.g., methylsulfonyloxy, ethylsulfonyloxy, propylsulfonyloxy, isopropylsulfonyloxy etc.), $C_{6-14}$ aryl-carbonyloxy (e.g., benzoyloxy etc.)], a nitro group, an alkoxy-carbonyl group (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl etc. and the like), an alkylamino group (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino etc., and the like), an alkoxyimino group (e.g., $C_{1-6}$ alkoxyimino such as methoxyimino, ethoxyimino, n-propoxyimino, tert-butoxyimino, n-hexyloxy-imino etc. and the like) and hydroxyimino.

When the above-mentioned hydrocarbon group is an aryl group or an aralkyl group, it may be substituted by 1 to 5 (preferably 1 to 3) of an alkyl group (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl etc., $C_{3-6}$ cycloalkyl such as cyclohexyl etc., and the like), an alkenyl group (e.g., $C_{2-6}$ alkenyl such as allyl, isopropenyl, isobutenyl, 1-methylallyl, 2-pentenyl, 2-hexenyl etc., and the like), an alkynyl group (e.g., $C_{2-6}$ alkynyl such as propargyl, 2-butynyl, 3-butynyl, 3-pentinyl, 3-hexynyl etc., and the like), an alkoxy group (e.g., $C_{1-6}$ alkoxy such as methoxy, ethoxy, n-propoxy, tert-butoxy, n-hexyloxy etc., and the like), an acyl group [e.g., $C_{1-7}$ alkanoyl such as formyl, acetyl, propionyl, butyryl, isobutyryl, pentanoyl, hexanoyl, heptanoyl etc.; $C_{6-14}$ aryl-carbonyl such as benzoyl, naphthalene carbonyl etc.; $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.; $C_{6-14}$ aryloxy-carbonyl such as phenoxycarbonyl etc.; $C_{7-19}$ aralkyl-carbonyl such as phenyl-$C_{1-4}$ alkylcarbonyl (e.g., benzylcarbonyl, phenethylcarbonyl, phenylpropylcarbonyl etc.), and the like; $C_{7-19}$ aralkyloxycarbonyl such as phenyl-$C_{1-4}$ alkyloxycarbonyl (e.g., benzyloxycarbonyl etc.), and the like], nitro, amino, hydroxy, cyano, sulfamoyl, mercapto, a halogen (e.g., fluorine, chlorine, bromine, iodine), and an alkylthio group ($C_{1-4}$ alkylthio such as methylthio, ethylthio, n-propylthio, isobutylthio etc., and the like).

The "acyl group" represented by $R^1$ is, for example, the "acyl" described in detail above as a substituent of the ring A.

The "acyloxy group" represented by $R^1$ is, for example, the "acyloxy" described in detail above as a substituent of the ring A.

Of those mentioned above, $R^1$ is preferably a hydrogen atom, an aralkyl group optionally having substituent(s), an acyl group, an acyloxy group or an alkyl group optionally having substituent(s), particularly preferably a hydrogen atom, an aralkyl group optionally having substituent(s), an acyl group or an acyloxy group.

The "aralkyl group" of the "aralkyl group optionally having substituent(s)" is preferably a $C_{7-16}$ aralkyl (e.g., $C_{6-10}$ aryl-$C_{1-6}$ alkyl such as benzyl, phenethyl etc., and the like), and the like. The "substituent" of the "aralkyl group optionally having substituent(s)" is preferably 1 to 4 substituents similar to the "substituent" of the aforementioned "alkyl optionally having substituent(s)". When the number of substituents is 2 or more, each substituent may be the same or different.

As $R^1$, particularly preferred is a hydrogen atom.

The "alkyl group optionally having substituent(s)" represented by $R^2$, $R^3$ or $R^4$ may be the "alkyl optionally having substituent(s)" described in detail above as the substituent of the ring A.

The "alkoxy group optionally having substituent(s)" represented by $R^2$, $R^3$ or $R^4$ may be the "alkoxy optionally having substituent(s)" described in detail above as the substituent of the ring A.

The "amino group optionally having substituent(s)" represented by $R^2$, $R^3$ or $R^4$ may be, for example, amino, a mono-$C_{1-6}$ alkylamino (e.g., methylamino, ethylamino etc.), a mono-$C_{6-14}$ arylamino (e.g., phenylamino, 1-naphthylamino, 2-naphthylamino etc.), a di-$C_{1-6}$ alkylamino (e.g., dimethylamino, diethylamino etc.), a di-$C_{6-14}$ arylamino (e.g., diphenylamino etc.), and the like.

$R^2$ is preferably $C_{1-6}$ alkyl, $C_{1-6}$ alkoxy, $C_{1-6}$ alkoxy-$C_{1-6}$ alkoxy or di-$C_{1-6}$ alkylamino, more preferably $C_{1-3}$ alkyl.

$R^3$ is preferably a hydrogen atom, $C_{1-6}$ alkoxy-$C_{1-6}$ alkoxy or optionally halogenated $C_{1-6}$ alkoxy, more preferably optionally halogenated $C_{1-3}$ alkoxy.

$R^4$ is preferably a hydrogen atom or $C_{1-6}$ alkyl, more preferably a hydrogen atom.

X is preferably a nitrogen atom.

Y is preferably a nitrogen atom.

Specific examples of compound (I) include 2-[[[3-methyl-4-(2,2,2-trifluoroethoxy)-2-pyridinyl]methyl]thio]-1H-benzimidazole, 5-methoxy-2-[[(4-methoxy-3,5-dimethyl-2-pyridinyl)methyl]thio] -1H-benzimidazole, 2-[[(3,5-dimethyl-4-methoxy-2-pyridinyl)methyl]thio]-5-methoxy-1H-benzimidazole, 2-[[[4-(3-methoxypropoxy)-3-methyl-2-pyridinyl]methyl]thio]-1H-benzimidazole•sodium salt, 5-difluoromethoxy-2-[[(3,4-dimethoxy-2-pyridinyl)methyl] thio] -1H-benzimidazole and the like.

Of these, 2-[[[3-methyl-4-(2,2,2-trifluoroethoxy)-2-pyridinyl]methyl]thio]-1H-benzimidazole is preferable.

As compound (I), preferred is a compound represented by the formula

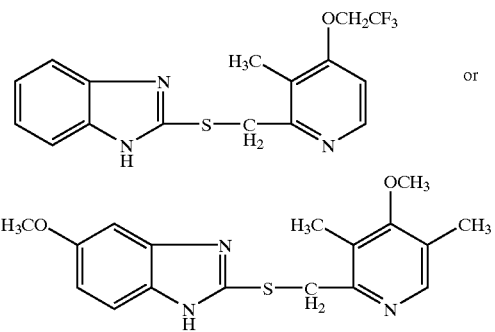

The salt of a compound represented by the formula (I) or the formula (II) is preferably a pharmaceutically acceptable salt, such as a salt with an inorganic base, a salt with an organic base, a salt with a basic amino acid, and the like.

Preferable examples of the salt with an inorganic base include alkali metal salts such as sodium salt, potassium salt and the like; alkaline earth metal salts such as calcium salt, magnesium salt and the like; ammonium salt and the like.

Preferable examples of the salt with an organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with a basic amino acid include salts with arginine, lysin, ornithine and the like.

Of these, preferred are alkali metal salt and alkaline earth metal salt. Particularly, sodium salt is preferable.

The compound (I) can be produced by a method known per se. In the case of, for example, 2-[[[3-methyl-4-(2,2,2-trifluoroethoxy)-2-pyridinyl]methyl]thio]-1H-benzimidazole or a salt thereof, a method described in JP-A-61-50978, U.S. Pat. No. 4,628,098, JP-A-10-195068, WO 98/21201 and the like and methods analogous thereto can be used for production.

According to the production method of the present invention, compound (I) is reacted with an excess amount of an oxidizing agent in the presence of a catalyst for asymmetric induction to give compound (II). Preferably, compound (I) and an excess amount of an oxidizing agent are reacted in the presence of a catalyst for asymmetric induction at about −20° C. to about 20° C., preferably about −10° C. to about 10° C., for about 0.1 to about 50 hr, preferably about 0.5 to about 10 hr to give compound (II).

Examples of the "oxidizing agent" include a peroxide (e.g., hydrogen peroxide, tert-butylhydroperoxide, cumene hydroperoxide etc.) and the like. Preferably, it is tert-butylhydroperoxide or cumene hydroperoxide, more preferably cumene hydroperoxide.

The amount of the "oxidizing agent" to be used need only be in excess of compound (I), and is, for example, about 1.5 to about 10 molar equivalents, preferably about 2 to about 10 molar equivalents, most preferably about 2 to about 5 molar equivalents, particularly preferably about 2.5 to about 4 molar equivalents.

The "catalyst for asymmetric induction" is, for example, an optically active titanium composite such as a complex of an optically active diol, titanium(IV) alkoxide and water, and the like. The "complex" may be prepared in advance and thereafter added to the reaction mixture, or may be formed in the reaction mixture.

Examples of the "optically active diol" include alkyldiol, aromatic diol and the like.

Examples of the "alkyldiol" include optically active tartrates such as dimethyl (+)- or (−)-tartrate, diethyl (+)- or (−)-tartrate, diisopropyl (+)- or (−)-tartrate, dibutyl (+)- or (−)-tartrate and the like, optically active ethanediols such as (R,R)- or (S,S)-diphenylethane-1,2-diol and the like.

Examples of the "aromatic diols" include optically active phenols such as (+)-, or (−)-binaphthol and the like.

Of these, preferred are diethyl (+)- or (−)-tartrate, diisopropyl (+)- or (−)-tartrate and the like.

The amount of the "optically active diol" to be used is about 1 to 10 molar equivalents, preferably about 2 to 5 molar equivalents, relative to titanium(IV) alkoxide.

Examples of the "titanium(IV) alkoxide" include titanium (IV) 2-ethylhexoxide, titanium(IV) butoxide, titanium(IV) propoxide, titanium(IV) isopropoxide, titanium(IV) ethoxide, titanium(IV) methoxide and the like. Preferred is titanium(IV) isopropoxide.

The amount of the "titanium(IV) alkoxide" to be used is about 0.001 to about 5 molar equivalents, preferably about 0.03 to about 2 molar equivalents, more preferably about 0.03 to about 1 molar equivalent, relative to compound (I).

The amount of "water" to be used in the complex is about 0.1 to 2 equivalents, preferably about 0.4 to 0.9 equivalent, relative to titanium(IV) alkoxide.

Water may be contained in the crystal of compound (I), in a reaction reagent (e.g., optically active diol etc.) or in a solvent, or may be added.

The total amount of the "water" present in the reaction mixture is about 0.1 to 2 equivalents, preferably about 0.4 to 0.9 equivalent, relative to titanium(IV) alkoxide.

In this reaction, a substance to adjust water content of the reaction mixture may be co-existent. In this case, the amount of water to be used may be outside the above-mentioned range. As the "substance to adjust water content of the reaction mixture", for example, a suitable amount of zeolite containing pores having a suitable size [e.g., molecular sieve (trade name)], aluminum phosphate, an inorganic ion exchange Montmorillonite intercalation compound, active carbon and the like is used.

One of the major characteristics of the present invention is that the amount of a catalyst for asymmetric induction, such as an optically active titanium composite and the like, can be reduced.

As a complex of the optically active diol, titanium(IV) alkoxide and water, a complex formed using the titanium (IV) alkoxide/optically active diol/water in a molar ratio of 1/about 1-about 10/about 0.1-about 2 (preferably a molar ratio of 1/about 2-about 5/about 0.4-about 0.9) is preferable.

In a preferable embodiment of the present invention, (1) the proportion of the amounts of titanium(IV) alkoxide and oxidizing agent to be used is preferably about 0.03 to about 1 molar equivalent and about 1.5 to about 10 molar equivalents, respectively, relative to 1 molar equivalent of the compound represented by the formula (I) or a salt thereof, which are reacted at about −20° C. to about 20° C., (2) the proportion of the amounts of titanium(IV) alkoxide and oxidizing agent to be used is more preferably about 0.03 to about 0.25 molar equivalent and about 2 to about 5 molar equivalents, respectively, relative to 1 molar equivalent of the compound represented by the formula (I) or a salt thereof, which are reacted at about −10° C. to about 10° C., and (3) the proportion of the amounts of titanium(IV) alkoxide and oxidizing agent to be used is particularly preferably about 0.05 to about 0.20 molar equivalent and about 2.5 to about 4 molar equivalents, respectively, relative to 1 molar equivalent of the compound represented by the formula (I) or a salt thereof, which are reacted at about −10° C. to about 10° C.

In this reaction, a base may be added where necessary.

Examples of the "base" include an inorganic base, an organic base, a basic amino acid and the like. Examples of the inorganic base include an alkali metal carbonate such as potassium carbonate, sodium carbonate and the like, an alkali metal hydroxide such as sodium hydroxide, potassium hydroxide and the like, an alkali metal hydride such as sodium hydride, potassium hydride and the like, and the like. Examples of the organic base include alkali metal alkoxides such as sodium methoxide, sodium ethoxide and the like, alkali metal carboxylic acid salts such as sodium acetate and the like, amines such as piperidine, piperazine, pyrrolidine, morpholine, triethylamine, tripropylamine, tributylamine, trioctylamine, diisopropylethylamine, dimethylphenylamine and the like, and pyridines such as pyridine, dimethylaminopyridine and the like. Examples of the basic amino acid include arginine, lysine, ornithine and the like. Of these, preferred are amines, which are exemplified by triethylamine, tripropylamine, diisopropylethylamine and trioctylamine.

The amount of the "base" to be used is about 0.01 to 10 molar equivalents, preferably about 0.1 to 1 molar equivalent, relative to compound (I).

This reaction is advantageously carried out without a solvent or in the presence of a solvent that does not influence the reaction. While the solvent is free of any particular limitation as long as the reaction proceeds, examples of the solvent include alcohols such as methanol, ethanol, propanol, isopropanol etc., aromatic hydrocarbons such as benzene, toluene, xylene etc., ethers such as diethylether, diisopropyl ether, butylmethylether, dioxane, tetrahydrofuran etc., esters such as ethyl acetate, methyl acetate etc., ketones such as acetone, methylisobutylketone etc., halogenated hydrocarbons such as chloroform, dichloromethane, ethylene dichloride, carbon tetrachloride etc., amides such as N,N-dimethylformamide etc., sulfoxides such as dimethylsulfoxide etc., acetic acid and the like. Of these solvents, toluene and ethyl acetate are particularly preferable.

This reaction is carried out in the atmosphere, under an inert gas atmosphere, or under an inert gas stream.

Examples of the "inert gas" include nitrogen, helium, neon, argon and the like.

Preferable examples of the production method of the present invention include a method comprising
(i) reacting compound (I) with an excess oxidizing agent in the presence of a catalyst for asymmetric induction, an organic solvent and a base at about −20 to 20° C., preferably about −10 to 10° C.,
(ii) reacting compound (I) with an excess oxidizing agent in the presence of a catalyst for asymmetric induction and an organic solvent at about −20 to 20° C., preferably about −10 to 10° C.,
(iii) reacting compound (I) with an excess oxidizing agent in the presence of a catalyst for asymmetric induction and a base at about −20 to 20° C., preferably about −10 to 10° C.,
(iv) reacting compound (I) with an excess oxidizing agent in the presence of a catalyst for asymmetric induction at about −20 to 20° C., preferably about −10 to 10° C., and the like. Of these, preferred is (i).

Preferable examples of this reaction include adding titanium(IV) alkoxide to a mixture of compound (I) and an optically active diol, and where necessary, water and an organic solvent, and adding a base and an oxidizing agent. The order of addition of compound (I), an optically active diol, water and an organic solvent may be any. The order of addition of a base and an oxidizing agent may be any. Preferably, a base is added and then an oxidizing agent is added.

In the above-mentioned reaction, it is preferable that titanium(IV) alkoxide be added and then the reaction mixture be stirred with heating. The temperature for heating is generally about 20° C. to 100° C., preferably 40 to 70° C. The time of stirring is generally about 0.05 to 12 hr, preferably about 0.2 to 3 hr. The temperature of addition of a base is about −40 to 100° C., preferably −20 to 70° C. Before addition of an oxidizing agent, the reaction mixture is cooled to about −40 to 40° C., preferably, −20 to 20° C. Thereafter, the reaction is carried out by stirring at about −20 to 20° C., preferably about −10 to 10° C., for about 0.1 to 50 hr, preferably, about 0.5 to 10 hr.

The thus-obtained compound (II) may be isolated according to a separation and purification means known per se, such as concentration, solvent extraction, crystallization, phase transfer, chromatography or a combination thereof and the like.

As the "chromatography", a chromatography using silica gel chemically modified with a basic group (e.g., aminopropyl group etc.) is preferable. Examples thereof include Daisogel IR-60-APS (trade name, produced by Daiso Co., Ltd.), YFLC gel $NH_2$ (amino) (trade name, produced by Yamazen Corporation) and the like.

The compound (II) is useful as a pharmaceutical product, because it has a superior antiulcer activity, a gastric acid secretion-inhibitory action, a mucosa-protecting action, an anti-*Helicobacter pylori* action and the like, and shows low toxicity. For example, compound (II) is useful for the prophylaxis or treatment of digestive ulcer (e.g., gastric ulcer, duodenal ulcer, anastomotic ulcer, Zollinger-Ellison syndrome etc.), gastritis, reflux esophagitis, NUD (Non Ulcer Dyspepsia), gastric cancer (including gastric cancer due to promoted production of interleukin-1β caused by genetic polymorphism of interleukin-1), gastric MALT lymphoma and the like, eradication of *Helicobacter pylori*, suppression of hemorrhage of upper gastrointestinal tract due to digestive ulcer, acute stress ulcer and hemorrhagic gastritis, suppression of hemorrhage of upper gastrointestinal tract caused by invasion stress (stress due to major surgery requiring intensive management after operation and cerebrovascular disorder, external injury in the head, multiple organ failure and extensive burn requiring intensive treatment), prophylaxis or treatment of ulcer caused by nonsteroidal antiinflammatory agent; prophylaxis or treatment of gastric hyperacidity and ulcer due to postoperative stress, pre-anesthetic administration and the like, in mammals (e.g., human, simian, sheep, cattle, horse, dog, cat, rabbit, rat, mouse etc.). For eradication of *Helicobacter pylori*, compound (II) and penicillin antibiotics (e.g., amoxicillin etc.) and erythromycin antibiotics (e.g., clarithromycin etc.) are preferably used.

EXAMPLES

The present invention is described in more detail in the following by means of Examples, which are not to be construed as limitative.

The enantiomer excess (% ee) was measured by high performance liquid chromatography using an optically active column under the following conditions (A).

The amounts of the sulfide form and sulfone form present were measured by high performance liquid chromatography using an optically active column under the following conditions (A) or high performance liquid chromatography under the conditions (B).

high performance liquid chromatography conditions (A);
column: CHIRALCEL OD (manufactured by Daicel Chemical Industries, Ltd.)
mobile phase: hexane/ethanol=90/10
flow rate: 1.0 ml/min
detection: UV285 nm
high performance liquid chromatography conditions (B);
column: Capcell Pak (manufactured by Shiseido Company, Ltd.)
mobile phase: obtained by adding phosphoric acid to an acetonitrile:water:triethylamine mixed solution (50:50:1) and adjusting to pH 7.0.
flow rate: 1.0 ml/min
detection: UV 285 nm

Example 1

Production of (R)-2-[[[3-methyl-4-(2,2,2-trifluoroethoxy)-2-pyridyl]methyl]sulfinyl]benzimidazole (1) Under a nitrogen atmosphere, 2-[[[3-methyl-4-(2,2,2-trifluoroethoxy)-2-pyridyl]methyl]thio]benzimidazole (50.0 g, 0.14 mol, containing 16.7 mg of water), toluene (250 ml), water (283 mg, 0.016 mol, total water content 0.017 mol) and diethyl (+)-tartrate (10.6 ml, 0.062 mol) were mixed and the mixture was stirred at 50 to 55° C. for 30 min. Under a nitrogen atmosphere, titanium(IV) isopropoxide (8.29 ml, 0.028 mol) was added, and the mixture was stirred at 50 to 55° C. for 1 hr. Under a nitrogen atmosphere and under cooling, diisopropylethylamine (8.13 ml, 0.047 mol) was added to the obtained mixture, and then cumene hydroperoxide (76.50 ml, content 82%, 0.43 mol) was added at −10 to 0° C. The mixture was allowed to react by stirring at −10 to 10° C. for 4.5 hr.

The reaction mixture was analyzed by high performance liquid chromatography (conditions (A)), and as a result, it was found that 0.74% of a sulfide form and 1.46% of a sulfone form were present as analogous substances in the reaction mixture, and other analogous substances were not present. The enantiomer excess of the title compound in the reaction mixture was 96.5% ee.

(2) To the reaction mixture obtained in (1) above was added a 30% aqueous sodium thiosulfate solution (180 ml) under a nitrogen atmosphere to decompose the residual cumene hydroperoxide. After partitioning, 75 ml of the obtained organic layer (375 ml) was used to perform the following experiment.

Water (5 ml), a heptane-diisopropyl ether mixture (1:2) (90 ml) and heptane (60 ml) were successively added to the organic layer (75 ml) and the mixture was stirred for 2 hr. The crystals were separated, washed with a mixture of toluene-diisopropyl ether (toluene:diisopropyl ether=1:4) (40 ml) and dried to give crystals (10.25 g, yield 98.1%).

The obtained crystals were analyzed by high performance liquid chromatography (conditions (A)). As a result, it was found that 1.5% of a sulfone form was present as an analogous substance in the crystals, and other analogous substances were not present. The enantiomer excess of the title compound in the reaction mixture was 100% ee.

Example 2

Production of (R)-2-[[[3-methyl-4-(2,2,2-trifluoroethoxy)-2-pyridyl]methyl]sulfinyl]benzimidazole (1) Under a nitrogen stream, 2-[[[3-methyl-4-(2,2,2-trifluoroethoxy)-2-pyridyl]methyl]thio]benzimidazole (900 g, 2.55 mol, containing 80 mg of water), toluene (4500 ml), water (5.4 g, 0.300 mol, total water content 0.304 mol) and diethyl (+)-tartrate (192 ml, 1.12 mol) were mixed and the mixture was stirred at 50–56° C. for 30 min. Under a nitrogen stream, titanium(IV) isopropoxide (149 ml, 0.505 mol) was added, and the mixture was stirred at 53 to 56° C. for 1 hr. Under a nitrogen stream, the mixture was cooled to room temperature, and diisopropylethylamine (147 ml, 0.844 mol) was added to the obtained mixture, and then cumene hydroperoxide (1380 ml, content 82%, 7.70 mol) was added at −5 to 5° C. The mixture was reacted by stirring at −5 to 5° C. for 2 hr.

The reaction mixture was analyzed by high performance liquid chromatography (conditions (A)). As a result, it was found that 1.37% of a sulfide form and 1.28% of a sulfone form were present as analogous substances in the reaction mixture, and other analogous substances were not present. The enantiomer excess of the title compound in the reaction mixture was 96.9% ee.

(2) To the reaction mixture obtained in the above-mentioned (1) was added a 30% aqueous sodium thiosulfate solution (3420 ml) under a nitrogen stream to decompose the residual cumene hydroperoxide. After partitioning, heptane (9000 ml) was added to the obtained organic layer to allow crystallization. The crystals were separated and washed with heptane-toluene (heptane:toluene=2:1) (4500 ml), which was followed by recrystallization from a mixture of acetone-water (acetone:water=1:3) (21150 ml) to give crystals.

The crystals were analyzed by high performance liquid chromatography (conditions (A)). As a result, it was found that 0.3% of a sulfide form and 0.7% of a sulfone form were present as analogous substances in the crystals, and other analogous substances were not present. The enantiomer excess of the title compound in the reaction mixture was 100% ee.

Example 3

Production of (R)-2-[[[3-methyl-4-(2,2,2-trifluoroethoxy)-2-pyridyl]methyl]sulfinyl]benzimidazole 2-[[[3-Methyl-4-(2,2,2-trifluoroethoxy)-2-pyridyl]methyl]thio]benzimidazole (25.0 g, 0.071 mol, containing 13.4 mg of water), toluene (122 ml), water (137 mg, 0.0076 mol, total water content 0.0083 mol) and diethyl (+)-tartrate (5.32 ml, 0.031 mol) were mixed. To the mixture was added titanium(IV) isopropoxide (4.15 ml, 0.014 mol) at 50 to 60° C., and the mixture was stirred at 50 to 55° C. for 1 hr. To the obtained mixture was added diisopropylethylamine (4.07 ml, 0.023 mol) at room temperature, and then cumene hydroperoxide (38.2 ml, content 82%, 0.22 mol) was added at −5 to 5° C. The mixture was reacted by stirring at −5 to 5° C. for 1.5 hr.

The reaction mixture was analyzed by high performance liquid chromatography (conditions (A)). As a result, it was found that 0.60% of a sulfide form and 1.76% of a sulfone form were present as analogous substances in the reaction mixture, and other analogous substances were not present. The enantiomer excess of the title compound in the reaction mixture was 97.2% ee.

The reaction mixture was quantitatively analyzed by high performance liquid chromatography (conditions (B)) (by comparison of area with standard product whose content is known). As a result, the yield of the title compound was 94.0%.

Example 4

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (20.0 g, 0.057 mol, containing 8.9 mg of water), toluene (100 ml), water (24 mg, 0.0013 mol, total water content 0.0018 mol) and diethyl (+)-tartrate (1.06 ml, 0.0062 mol) were mixed, and the mixture was stirred at 50–55° C. for 30 min. Under a nitrogen atmosphere, to the mixture was added titanium(IV) isopropoxide (0.83 ml, 0.0028 mol), and the mixture was stirred at 50 to 55° C. for 30 min. Under a nitrogen atmosphere and under cooling, to the obtained mixture was added diisopropylethylamine (3.25 ml, 0.019 mol), and then cumene hydroperoxide (30.6 ml, content 82%, 0.17 mol) was added at −5 to 0° C. The mixture was reacted by stirring at −5 to 0° C. for 5.5 hr.

The reaction mixture was analyzed by high performance liquid chromatography (conditions (A)). As a result, the enantiomer excess of the title compound in the reaction mixture was 95.7% ee.

Example 5

Production of (S)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol, containing 2.2 mg of water), toluene (25 ml), water (28 mg, 0.0016 mol, total water content 0.0017 mol) and diethyl (−)-tartrate (1.06 ml, 0.0062 mol) were mixed, and the mixture was stirred at 50 to 55° C. for 30 min. Under a nitrogen atmosphere, titanium(IV) isopropoxide (0.83 ml, 0.0028 mol) was added and the mixture was stirred at 50 to 55° C. for 30 min. Under a nitrogen atmosphere and under cooling, to the obtained mixture was added diisopropylethylamine (0.81 ml, 0.0047 mol), and then cumene hydroperoxide (7.65 ml, content 82%, 0.043 mol) was added at −5 to 0° C. The mixture was reacted by stirring at −5 to 0° C. for 2 hr.

The reaction mixture was analyzed by high performance liquid chromatography (conditions (A)). As a result, it was found that 1.16% of a sulfide form and 1.51% of a sulfone form were present as analogous substances in the reaction mixture, and other analogous substances were not present. The enantiomer excess of the title compound in the reaction mixture was 96.8% ee.

Example 6

Production of (R)-2-[[[3-methyl-4-(2,2,2-trifluoroethoxy)-2-pyridyl]methyl]sulfinyl]benzimidazole Under a nitrogen stream, 2-[[[3-methyl-4-(2,2,2-trifluoroethoxy)-2-pyridyl]methyl]thio]benzimidazole (4.5 kg, 12.7 mol, containing 1.89 g of water), toluene (22 L), water (25 g, 1.39 mol, total water content 1.49 mol) and diethyl (+)-tartrate (0.958 L, 5.60 mol) were mixed. Under a nitrogen stream, titanium(IV) isopropoxide (0.747 L, 2.53 mol) was added to the mixture at 50 to 60° C., and the mixture was stirred at the same temperature for 30 min. Under a nitrogen stream, diisopropylethylamine (0.733 L, 4.44 mol) was added to the mixture at room temperature, and then cumene hydroperoxide (6.88 L, content 82%, 37.5 mol) was added at −5 to 5° C. The mixture was reacted by stirring at −5 to 5° C. for 1.5 hr.

The reaction mixture was analyzed by high performance liquid chromatography (conditions (B)). As a result, it was found that 1.87% of a sulfide form and 1.59% of a sulfone form were present as analogous substances in the reaction mixture, and other analogous substances were not present.

(2) To the reaction mixture obtained in the above-mentioned (1) was added 30% aqueous sodium thiosulfate solution (17 L) under a nitrogen stream to decompose the residual cumene hydroperoxide. After partitioning, water (4.5 L), heptane (40.5 L) and t-butyl methyl ether (18 L) were added to the obtained organic layer to allow crystallization. The crystals were separated and washed with t-butylmethylether-toluene (t-butylmethylether:toluene= 4:1)(4 L).

The obtained crystals were analyzed by high performance liquid chromatography (conditions (A)). As a result, it was found that 0.90% of a sulfide form was present as an analogous substance in the reaction mixture, and a sulfide form and other analogous substances were not present. The enantiomer excess of the title compound in the reaction mixture was 100% ee.

Example 7

Production of (R)-2-[[[3-methyl-4-(2,2,2-trifluoroethoxy)-2-pyridyl]methyl]sulfinyl]benzimidazole 2-[[[3-Methyl-4-(2,2,2-trifluoroethoxy)-2-pyridyl]methyl]thio]benzimidazole (50.0 g, 0.14 mol), toluene (244 ml), water (233 mg, 0.013 mol, total water content 0.013 mol) and diethyl (+)-tartrate (10.6 ml, 0.062 mol) were mixed, and titanium(IV) isopropoxide (8.3 ml, 0.025 mol) was added at 50 to 60° C. The mixture was stirred at 50 to 60° C. for 30 min. Diisopropylethylamine (8.14 ml, 0.047 mol) was added to the obtained mixture at room temperature and then cumene hydroperoxide (76.4 ml, content 82%, 0.43 mol) was added at −5 to 5° C. The mixture was reacted by stirring at −5 to 5° C. for 1.5 hr.

The reaction mixture was analyzed by high performance liquid chromatography (conditions (B)). As a result, it was found that 1.31% of a sulfide form and 1.70% of a sulfone form were present as analogous substances in the reaction mixture, and other analogous substances were not present.

The reaction mixture was analyzed by high performance liquid chromatography (conditions (A)). As a result, the enantiomer excess of the title compound in the reaction mixture was 96% ee.

Example 8

Production of (R)-2-[[[3-methyl-4-(2,2,2-trifluoroethoxy)-2-pyridyl]methyl]sulfinyl]benzimidazole 2-[[[3-Methyl-4-(2,2,2-trifluoroethoxy)-2-pyridyl]methyl]thio]benzimidazole (25.0 g, 0.071 mol, containing 13.4 mg of water), toluene (122 ml), water (162 mg, 0.0076 mol, total water content 0.00973 mol) and diethyl (+)-tartrate (5.32 ml, 0.031 mol) were mixed, and titanium(IV) isopropoxide (4.15 ml, 0.014 mol) was added to the mixture at 50 to 60° C. The mixture was stirred at 50 to 55° C. for 1 hr. Diisopropylethylamine (4.07 ml, 0.023 mol) was added to the obtained mixture at room temperature, and then cumene hydroperoxide (38.2 ml, content 82%, 0.22 mol) was added at 0 to 10° C. The mixture was reacted by stirring at 0 to 5° C. for 1.5 hr.

The reaction mixture was analyzed by high performance liquid chromatography (conditions (B)). As a result, it was found that 1.14% of a sulfide form and 1.8% of a sulfone form were present as analogous substances in the reaction mixture, and other analogous substances were not present.

The reaction mixture was analyzed by high performance liquid chromatography (conditions (A)). As a result, the enantiomer excess of the title compound in the reaction mixture was 96% ee.

Example 9

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (50.0 g, 0.14 mol, containing 16.7 mg of water), toluene (100 ml), water (283 mg, 0.016 mol, total water content 0.017 mol) and diethyl (+)-tartrate (10.6 ml, 0.062 mol) were mixed, and the mixture was stirred at 50 to 55° C. for 30 min. Titanium(IV) isopropoxide (8.29 ml, 0.028 mol) was added to the mixture under a nitrogen atmosphere, and the mixture was stirred at 50 to 55° C. for 1 hr. Under a nitrogen atmosphere and under cooling, to the obtained mixture was added diisopropylethylamine (8.13 ml, 0.047 mol) and then cumene hydroperoxide (76.50 ml, content 82%, 0.43 mol) was added at −10 to 0° C. The mixture was reacted by stirring at 0 to 10° C. for 5.5 hr.

The reaction mixture was analyzed by high performance liquid chromatography (conditions (B)). As a result, it was found that 2.1% of a sulfide form and 1.9% of a sulfone form were present as analogous substances in the reaction mixture, and other analogous substances were not present.

The reaction mixture was analyzed by high performance liquid chromatography (conditions (A)). As a result, the enantiomer excess of the title compound in the reaction mixture was 95.3% ee.

Example 10

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol, containing 2.2 mg of water), water (140 mg, 0.0078 mol, total water content 0.0079 mol) and diethyl (+)-tartrate (5.31 ml, 0.031 mol) were mixed, and the mixture was stirred at 50 to 55° C. for 30 min. Under a nitrogen atmosphere, titanium(IV) isopropoxide (4.14 ml, 0.014 mol) was added, and the mixture was stirred at 50 to 55° C. for 1 hr. Under a nitrogen atmosphere and under cooling, to the obtained mixture was added diisopropylethylamine (0.81 ml, 0.0047 mol) and then cumene hydroperoxide (7.65 ml, content 82%, 0.043 mol) was added at −5 to 10° C. The mixture was reacted by stirring at 0 to 10° C. for 3.5 hr.

The reaction mixture was analyzed by high performance liquid chromatography (conditions (A)). As a result, it was found that 1.7% of a sulfide form and 5.3% of a sulfone form were present as analogous substances in the reaction mixture, and other analogous substances were not present. The enantiomer excess of the title compound in the reaction mixture was 89.4% ee.

Example 11

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (50.0 g, 0.14 mol, containing 16.7 mg of water), ethyl acetate (244 ml), water (274 mg, 0.015 mol, total water content 0.016 mol) and diethyl (+)-tartrate (10.6 ml, 0.062 mol) were mixed, and the mixture was stirred at 50 to 55° C. for 30 min. Under a nitrogen atmosphere, titanium(IV) isopropoxide (8.3 ml, 0.028 mol) was added to the mixture, and the mixture was stirred at 50 to 55° C. for 1 hr. Under a nitrogen atmosphere and under cooling, diisopropylethylamine (8.14 ml, 0.047 mol) was added to the obtained mixture and then cumene hydroperoxide (76.4 ml, content 82%, 0.43 mol) was added at −10 to 0° C. The mixture was reacted by stirring at 0 to 5° C. for 3 hr.

The reaction mixture was analyzed by high performance liquid chromatography (conditions (B)). As a result, it was found that 3% of a sulfide form and 2% of a sulfone form were present as analogous substances in the reaction mixture, and other analogous substances were not present.

The reaction mixture was analyzed by high performance liquid chromatography (conditions (A)). As a result, the enantiomer excess of the title compound in the reaction mixture was 95.1% ee.

Example 12

Production of (S)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (50.0 g, 0.14 mol), toluene (250 ml), water (130 mg, 0.0072 mol, total water content 0.0072 mol) and diethyl (−)-tartrate (5.31 ml, 0.031 mol) were mixed. Under a nitrogen atmosphere, titanium(IV) isopropoxide (4.1 ml, 0.014 mol) was added at 50° C. and the mixture was stirred at 50 to 55° C. for 30 min. Under a nitrogen atmosphere and under cooling, to the obtained mixture was added diisopropylethylamine (8.13 ml, 0.047 mol), and then cumene hydroperoxide (76.5 ml, content 82%, 0.42 mol) was added at −10 to 0° C. The mixture was reacted by stirring at 0 to 5° C. for 3.5 hr.

The reaction mixture was analyzed by high performance liquid chromatography (conditions (A)). As a result, it was found that 1.39% of a sulfide form and 1.50% of a sulfone form were present as analogous substances in the reaction mixture, and other analogous substances were not present. The enantiomer excess of the title compound in the reaction mixture was 96.5% ee.

Example 13

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (20.0 g, 0.057 mol), toluene (100 ml), water (110 mg, 0.0061 mol, total water content 0.0061 mol) and diethyl (+)-tartrate (4.25 ml, 0.025 mol) were mixed, and the mixture was stirred at 50 to 55° C. for 30 min. Under a nitrogen atmosphere, titanium(IV) isopropoxide (3.32 ml, 0.011 mol) was added to the mixture, and the mixture was stirred at 50 to 55° C. for 90 min. Under a nitrogen atmosphere and under cooling, to the obtained mixture was added diisopropylethylamine (3.25 ml, 0.019 mol) and then cumene hydroperoxide (20.4 ml, content 82%, 0.11 mol) was added at 0 to 5° C. The mixture was reacted by stirring at 0 to 5° C. for 6 hr.

The reaction mixture was analyzed by high performance liquid chromatography (conditions (B)). As a result, it was found that 1.0% of a sulfide form and 2.0% of a sulfone form were present as analogous substances in the reaction mixture, and other analogous substances were not present.

The reaction mixture was analyzed by high performance liquid chromatography (conditions (A)). As a result, the enantiomer excess of the title compound in the reaction mixture was 96.6% ee.

Example 14

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (20.0 g, 0.057 mol), toluene (100 ml), water (110 mg, 0.0061 mol, total water content 0.0061 mol) and diethyl (+)-tartrate (4.25 ml, 0.025 mol) were mixed, and the mixture was stirred at 50 to 55° C. for 30 min. Under a nitrogen atmosphere, titanium(IV) isopropoxide (3.32 ml, 0.011 mol) was added to the mixture and the mixture was stirred at 50 to 55° C. for 90 min. Under a nitrogen atmosphere and under cooling, to the obtained mixture was added diisopropylethylamine (3.25 ml, 0.019 mol) and then cumene hydroperoxide (51.0 ml, content 82%, 0.283 mol) was added at 0 to 5° C. The mixture was reacted by stirring at 0 to 5° C. for 6.5 hr.

The reaction mixture was analyzed by high performance liquid chromatography (conditions (A)). As a result, it was found that 0.98% of a sulfide form and 3.65% of a sulfone form were present as analogous substances in the reaction mixture, and other analogous substances were not present. The enantiomer excess of the title compound in the reaction mixture was 90.9% ee.

Example 15

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (20.0 g, 0.057 mol), toluene (100 ml), water (55 mg, 0.0031 mol, total water content 0.0031 mol) and diethyl (+)-tartrate (2.12 ml, 0.012 mol) were mixed, and the mixture was stirred at 50 to 55° C. for 30 min. Under a nitrogen atmosphere, titanium(IV) isopropoxide (1.66 ml, 0.0057 mol) was added to the mixture, and the mixture was stirred at 50 to 55° C. for 1 hr. Under a nitrogen atmosphere and under cooling, to the obtained mixture was added diisopropylethylamine (3.25 ml, 0.019 mol) and then cumene hydroperoxide (30.6 ml, content 82%, 0.17 mol) was added at 0 to 5° C. The mixture was reacted by stirring at 0 to 5° C. for 3.5 hr.

The reaction mixture was analyzed by high performance liquid chromatography (conditions (A)). As a result, it was found that 1.32% of a sulfide form and 1.81% of a sulfone form were present as analogous substances in the reaction mixture, and other analogous substances were not present. The enantiomer excess of the title compound in the reaction mixture was 96.4% ee.

Example 16

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol), toluene (35 mL), water (28 mg, 0.0016 mol, total water content 0.0017 mol) and diethyl (+)-tartrate (1.33 mL, 0.0078 mol) were mixed, and the mixture was stirred at 50–55° C. for 30 min. Under a nitrogen atmosphere, titanium(IV) isopropoxide (1.04 mL, 0.0035 mol) was added to the mixture, and the mixture was stirred at 50 to 55° C. for 1 hr. Under a nitrogen atmosphere and under cooling, to the obtained mixture was added tripropylamine (0.89 mL, 0.0047 mol) and then cumene hydroperoxide (3.78 mL, 0.021 mol) was added at 15 to 20° C. The mixture was reacted by stirring at 15 to 20° C. for 1.5 hr.

The reaction mixture was analyzed by high performance liquid chromatography (conditions (A)). As a result, it was found that 3.7% of a sulfide form and 3.5% of a sulfone form were present as analogous substances in the reaction mixture, and other analogous substances were not present. The enantiomer excess of the title compound in the reaction mixture was 97.0% ee.

Example 17

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol), toluene (35 mL), water (28 mg, 0.0016 mol, total water content 0.0017 mol) and diethyl (+)-tartrate (1.33 mL, 0.0078 mol) were mixed, and the mixture was stirred at 50 to 55° C. for 30 min. Under a nitrogen atmosphere, titanium(IV) isopropoxide (1.04 mL, 0.0035 mol) was added to the mixture, and the mixture was stirred at 50 to 55° C. for 1 hr. Under a nitrogen atmosphere and under cooling, to the obtained mixture was added trioctylamine (2.04 mL, 0.0047 mol) and then cumene hydroperoxide (3.78 mL, 0.021 mol) was added at 15 to 20° C. The mixture was reacted by stirring at 15 to 20° C. for 1.5 hr.

The reaction mixture was analyzed by high performance liquid chromatography (conditions (A)). As a result, it was found that 5.4% of a sulfide form and 5.4% of a sulfone form were present as analogous substances in the reaction mixture, and other analogous substances were not present. The enantiomer excess of the title compound in the reaction mixture was 98.1% ee.

Example 18

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol), toluene (35 mL), water (28 mg, 0.0016 mol, total water content 0.0017 mol) and dimethyl (+)-tartrate (1.39 g, 0.0078 mol) were mixed, and the mixture was stirred at 50 to 55° C. for 40 min. Under a nitrogen atmosphere, titanium(IV) isopropoxide (1.04 mL, 0.0035 mol) was added to the mixture, and the mixture was stirred at 50 to 55° C. for 1 hr. Under a nitrogen atmosphere and under cooling, to the obtained mixture was added diisopropylethylamine (0.81 mL, 0.0047 mol) and then cumene hydroperoxide (3.78 mL, 0.021 mol) was added at 15 to 20° C. The mixture was reacted by stirring at 15 to 20° C. for 1.5 hr.

The reaction mixture was analyzed by high performance liquid chromatography (conditions (A)). As a result, it was found that 3.7% of a sulfide form and 3.5% of a sulfone form were present as analogous substances in the reaction mixture, and other analogous substances were not present. The enantiomer excess of the title compound in the reaction mixture was 94.7% ee.

Example 19

Production of (R)-2-[[[3-methyl-4-(2,2,2-trifluoroethoxy)-2-pyridyl]methyl]sulfinyl]benzimidazole Under a nitrogen atmosphere, 2-[[[3-methyl-4-(2,2,2-trifluoroethoxy)-2-pyridyl]methyl]thio]benzimidazole (5.00 g, 0.014 mol), toluene (35 mL), water (28 mg, 0.0016 mol, total water content 0.0017 mol) and dibutyl (+)-tartrate (1.87 mL, 0.0078 mol) were mixed, and the mixture was stirred at 50 to 55° C. for 40 min. Under a nitrogen atmosphere, titanium(IV) isopropoxide (1.04 mL, 0.0035 mol) was added to the mixture, and the mixture was stirred at 50 to 55° C. for 1 hr. Under a nitrogen atmosphere and under cooling, to the obtained mixture was added diisopropylethylamine (0.81 mL, 0.0047 mol) and then cumene hydroperoxide (3.78 mL, 0.021 mol) was added at 15 to 20° C. The mixture was reacted by stirring at 15 to 20° C. for 1.5 hr.

The reaction mixture was analyzed by high performance liquid chromatography (conditions (A)). As a result, it was found that 3.7% of a sulfide form and 3.5% of a sulfone form were present as analogous substances in the reaction mixture, and other analogous substances were not present. The enantiomer excess of the title compound in the reaction mixture was 98.7% ee.

INDUSTRIAL APPLICABILITY

According to the production method of the present invention, the objective optically active sulfoxide derivative (e.g., compound (II)) can be efficiently produced in high yield on an industrial large scale by a convenient method, while achieving an extremely high enantiomer excess and an extremely low amount of analogous substance present therein.

What is claimed is:

1. A method for producing an optically active form of a compound represented by the formula (II):

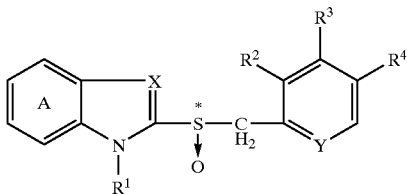

wherein ring A is a benzene ring optionally having 1 to 3 substituent(s) selected from (a) a halogen atom, (b) a cyano, (c) a nitro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group, $R^1$ is a hydrogen atom; a hydrocarbon group selected from (A) an alkyl group, an alkenyl group and an alkynyl group, each of which optionally has 1 to 3 substituent(s) selected from (a) an alkylthio group, (b) a halogen, (c) an alkoxy group, (d) an acyloxy group, (e) a nitro group, (f) an alkoxy-carbonyl group, (g) an alkylamino group, (h) an alkoxyimino group and (i) a hydroxyimino, and (B) an aryl group and an aralkyl group, each of which optionally has 1 to 5 substituent(s) selected from (a) an alkyl group, (b) an alkenyl group, (c) an alkynyl group, (d) an alkoxy group, (e) an acyl group, (f) a nitro, (g) an amino, (h) a hydroxy, (i) a cyano, (j) a sulfamoyl, (k) a mercapto, (l) a halogen and (m) an alkylthio group; an acyl group or an acyloxy group, $R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino, X is a nitrogen atom or CH, Y is a nitrogen atom or CH, and

* is an asymmetric center, or a salt thereof, comprising reacting a compound represented by the formula (I):

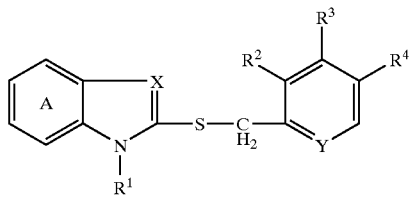

wherein each symbol is as defined above, or a salt thereof, with an excess amount of an oxidizing agent in the presence of a catalyst for asymmetric induction and a base;

wherein the amount of the oxidizing agent to be used is about 1.5 to about 10 molar equivalents relative to the compound represented by the formula (I) or a salt thereof.

2. A method for producing an optically active form of a compound represented by the formula (II):

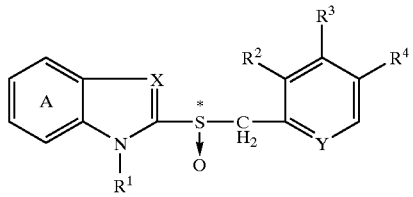

wherein ring A is a benzene ring optionally having 1 to 3 substituent(s) selected from (a) a halogen atom, (b) a cyano, (c) a nitro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group, $R^1$ is a hydrogen atom; a hydrocarbon group selected from (A) an alkyl group, an alkenyl group and an alkynyl group, each of which optionally has 1 to 3 substituent(s) selected from (a) an alkylthio group, (b) a halogen, (c) an alkoxy group, (d) an acyloxy group, (e) a nitro group, (f) an alkoxy-carbonyl group, (g) an alkylamino group, (h) an alkoxyimino group and (i) a hydroxyimino, and (B) an aryl group and an aralkyl group, each of which optionally has 1 to 5 substituent(s) selected from (a) an alkyl group, (b) an alkenyl group, (c) an alkynyl group, (d) an alkoxy group, (e) an acyl group, (f) a nitro, (g) an amino, (h) a hydroxy, (i) a cyano, (j) a sulfamoyl, (k) a mercapto, (l) a halogen and (m) an alkylthio group; an acyl group or an acyloxy group, $R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino, X is a nitrogen atom or CH, Y is a nitrogen atom or CH, and

* is an asymmetric center, or a salt thereof, comprising reacting a compound represented by the formula (I):

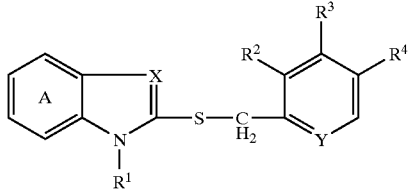

wherein each symbol is as defined above, or a salt thereof, with an excess amount of an oxidizing agent in the presence of a catalyst for asymmetric induction and a base;

wherein the amount of the oxidizing agent to be used is about 2.5 to about 4 molar equivalents relative to the compound represented by the formula (I) or a salt thereof.

3. The method according to claim 1, wherein the reaction is carried out at about −20° C. to about 20° C.

4. The method according to claim 1, wherein the reaction is carried out at about −10° C. to about 10° C.

5. The method according to claim 1, wherein the catalyst for the asymmetric induction is an optically active titanium composite.

6. The method according to claim 5, wherein the composite is a complex comprising an optically active diol, titanium(IV) alkoxide and water.

7. The method according to claim 6, wherein the complex is formed using titanium(IV) alkoxide/optically active diol/water in a molar ratio of 1/about 1 to about 10/about 0.1 to about 2.

8. The method according to claim 6, wherein the titanium (IV) alkoxide and the oxidizing agent are used in an amount of about 0.03 to about 1 molar equivalent and about 1.5 to about 10 molar equivalents, respectively, relative to 1 molar equivalent of the compound represented by the formula (I) or a salt thereof, and the reaction is carried out at about −20° C. to about 20° C.

9. The method according to claim 1, wherein the compound represented by the formula (II) is a compound represented by the formula:

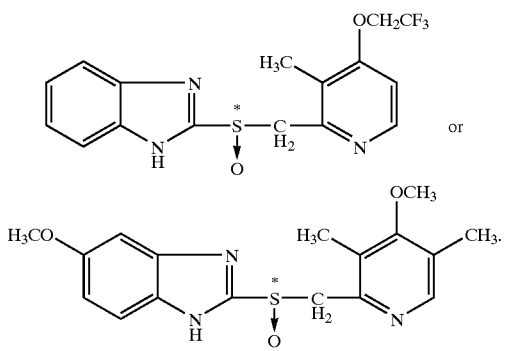

or

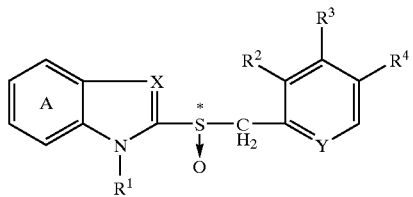

10. A method for producing an optically active form of a compound represented by the formula (II):

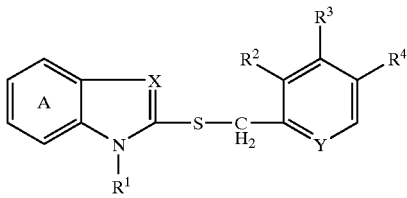

wherein
ring A is a benzene ring optionally having 1 to 3 substituent(s) selected from (a) a halogen atom, (b) a cyano, (c) a nitro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group,
$R^1$ is a hydrogen atom; an aralkyl group which optionally has 1 to 4 substituent(s) selected from a halogen atom, a hydroxy, a $C_{1-6}$ alkoxy, a $C_{1-6}$ alkoxy-carbonyl and a carbamoyl; an acyl group or an acyloxy group,
$R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino,
X is a nitrogen atom or CH,
Y is a nitrogen atom or CH, and
* is an asymmetric center,
or a salt thereof,
comprising reacting a compound represented by the formula (I):

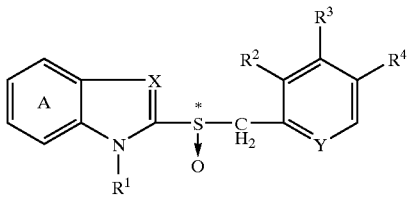

wherein each symbol is as defined above, or a salt thereof,
with an excess amount of an oxidizing agent in the presence of a catalyst for asymmetric induction and a base;
wherein the amount of the oxidizing agent to be used is about 1.5 to about 10 molar equivalents relative to the compound represented by the formula (I) or a salt thereof.

11. A method for producing an optically active form of a compound represented by the formula (II):

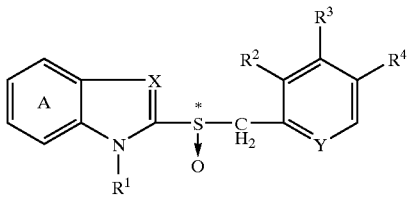

wherein
ring A is a benzene ring optionally having 1 to 3 substituent(s) selected from (a) a halogen atom, (b) a cyano, (c) a nitro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group,
$R^1$ is a hydrogen atom; a hydrocarbon group selected from (A) an alkyl group, an alkenyl group and an alkynyl group, each of which optionally has 1 to 3 substituent(s) selected from (a) an alkylthio group, (b) a halogen, (c) an alkoxy group, (d) an acyloxy group, (e) a nitro group, (f) an alkoxy-carbonyl group, (g) an alkylamino group, (h) an alkoxyimino group and (i) a hydroxyimino, and (B) an aryl group and an aralkyl group, each of which optionally has 1 to 5 substituent(s) selected from (a) an alkyl group, (b) an alkenyl group, (c) an alkynyl group, (d) an alkoxy group, (e) an acyl group, (f) a nitro, (g) an amino, (h) a hydroxy, (i) a cyano, (j) a sulfamoyl, (k) a mercapto, (l) a halogen and (m) an alkylthio group; an acyl group or an acyloxy group,
$R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino, X is a nitrogen atom or CH, Y is a nitrogen atom or CH, and

* is an asymmetric center, or a salt thereof, comprising reacting a compound represented by the formula (I):

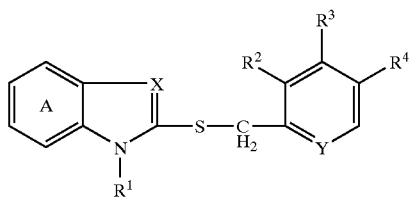

wherein each symbol is as defined above, or a salt thereof, with an excess amount of cumene hydroperoxide in the presence of a catalyst for asymmetric induction and a base;

wherein the amount of cumene hydroperoxide to be used is about 1.5 to about 10 molar equivalents relative to the compound represented by the formula (I) or a salt thereof.

12. A method for producing an optically active form of a compound represented by the formula (II):

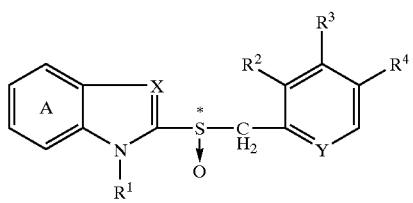

wherein ring A is a benzene ring optionally having 1 to 3 substituent(s) selected from (a) a halogen atom, (b) a cyano, (c) a nitro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group, $R^1$ is a hydrogen atom; a hydrocarbon group selected from (A) an alkyl group, an alkenyl group and an alkynyl group, each of which optionally has 1 to 3 substituent(s) selected from (a) an alkylthio group, (b) a halogen, (c) an alkoxy group, (d) an acyloxy group, (e) a nitro group, (f) an alkoxy-carbonyl group, (g) an alkylamino group, (h) an alkoxyimino group and (i) a hydroxyimino, and (B) an aryl group and an aralkyl group, each of which optionally has 1 to 5 substituent(s) selected from (a) an alkyl group, (b) an alkenyl group, (c) an alkynyl group, (d) an alkoxy group, (e) an acyl group, (f) a nitro, (g) an amino, (h) a hydroxy, (i) a cyano, (j) a sulfamoyl, (k) a mercapto, (l) a halogen and (m) an alkylthio group; an acyl group or an acyloxy group, $R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino, X is a nitrogen atom or CH, Y is a nitrogen atom or CH, and

* is an asymmetric center, or a salt thereof, comprising reacting a compound represented by the formula (I):

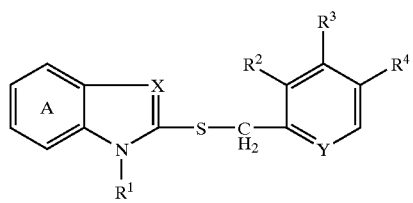

wherein each symbol is as defined above, or a salt thereof, with an excess amount of cumene hydroperoxide in the presence of a catalyst for asymmetric induction and a base;

wherein the amount of cumene hydroperoxide to be used is about 2.5 to about 4 molar equivalents relative to the compound represented by the formula (I) or a salt thereof.

13. A method for producing an optically active form of a compound represented by the formula (II):

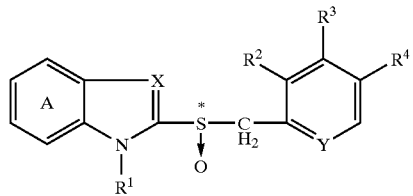

wherein ring A is a benzene ring optionally having 1 to 3 substituent(s) selected from (a) a halogen atom, (b) a cyano, (c) a intro, (d) an alkyl optionally having 1 to 3 substituent(s) selected from a halogen atom, a hydroxy, a $C_{1-6}$ alkoxy, a $C_{1-6}$ alkoxy-carbonyl and a carbamoyl, (e) a hydroxy, (f) an alkoxy optionally having 1 to 3 substituent(s) selected from a halogen atom, a hydroxy, a $C_{1-6}$ alkoxy, a $C_{1-6}$ alkoxy-carbonyl and a carbamoyl, (g) an aryl, (h) an aryloxy, (i) a carboxy, (j) an acyl, (k) an acyloxy and (l) a 5- to 10-membered heterocyclic group, $R^1$ is a hydrogen atom; a hydrocarbon group selected from (A) an alkyl group, an alkenyl group and an alkynyl group, each of which optionally has 1 to 3 substituent(s) selected from (a) an alkylthio group, (b)

a halogen, (c) an alkoxy group, (d) an acyloxy group, (e) a nitro group, (f) an alkoxy-carbonyl group, (g) an alkylamino group, (h) an alkoxyimino group and (i) a hydroxyimino, and (B) an aryl group and an aralkyl group, each of which optionally has 1 to 5 substituent(s) selected from (a) an alkyl group, (b) an alkenyl group, (c) an alkynyl group, (d) an alkoxy group, (e) an acyl group, (f) a nitro, (g) an amino, (h) a hydroxy, (i) a cyano, (j) a sulfamoyl, (k) a mercapto, (l) a halogen and (m) an alkylthio group; an acyl group or an acyloxy group, $R^2$, $R^3$ and $R^4$ are each a hydrogen atom; an alkyl group optionally having 1 to 3 substituent(s) selected from a halogen atom, a hydroxy, a $C_{1-6}$ alkoxy, a $C_{1-6}$ alkoxy-carbonyl and a carbamoyl; an alkoxy group optionally having 1 to 3 substituent(s) selected from a halogen atom, a hydroxy, a $C_{1-6}$ alkoxy, a $C_{1-6}$ alkoxy-carbonyl and a carbamoyl; an amino; a mono-$C_{1-6}$ alkylamino; a mono-$C_{6-14}$ arylamino; a di-$C_{1-6}$ alkylamino or a di-$C_{6-14}$ arylamino, X is a nitrogen atom or CH, Y is a nitrogen atom or CH, and

* is an asymmetric center, or a salt thereof, comprising reacting a compound represented by the formula (I):

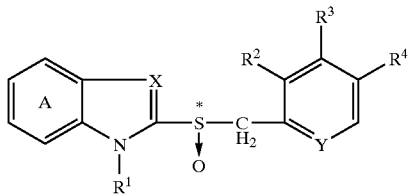

wherein each symbol is as defined above, or a salt thereof, with an excess amount of an oxidizing agent in the presence of a complex comprising an optically active diol, titanium(IV) alkoxide and water, and a base;

wherein the amount of the oxidizing agent to be used is about 1.5 to about 10 molar equivalents relative to the compound represented by the formula (I) or a salt thereof, and the total amount of the water present in the reaction mixture is about 0.1 to 2 equivalents relative to the titanium(IV) alkoxide.

* * * * *